Figures 1, 2:
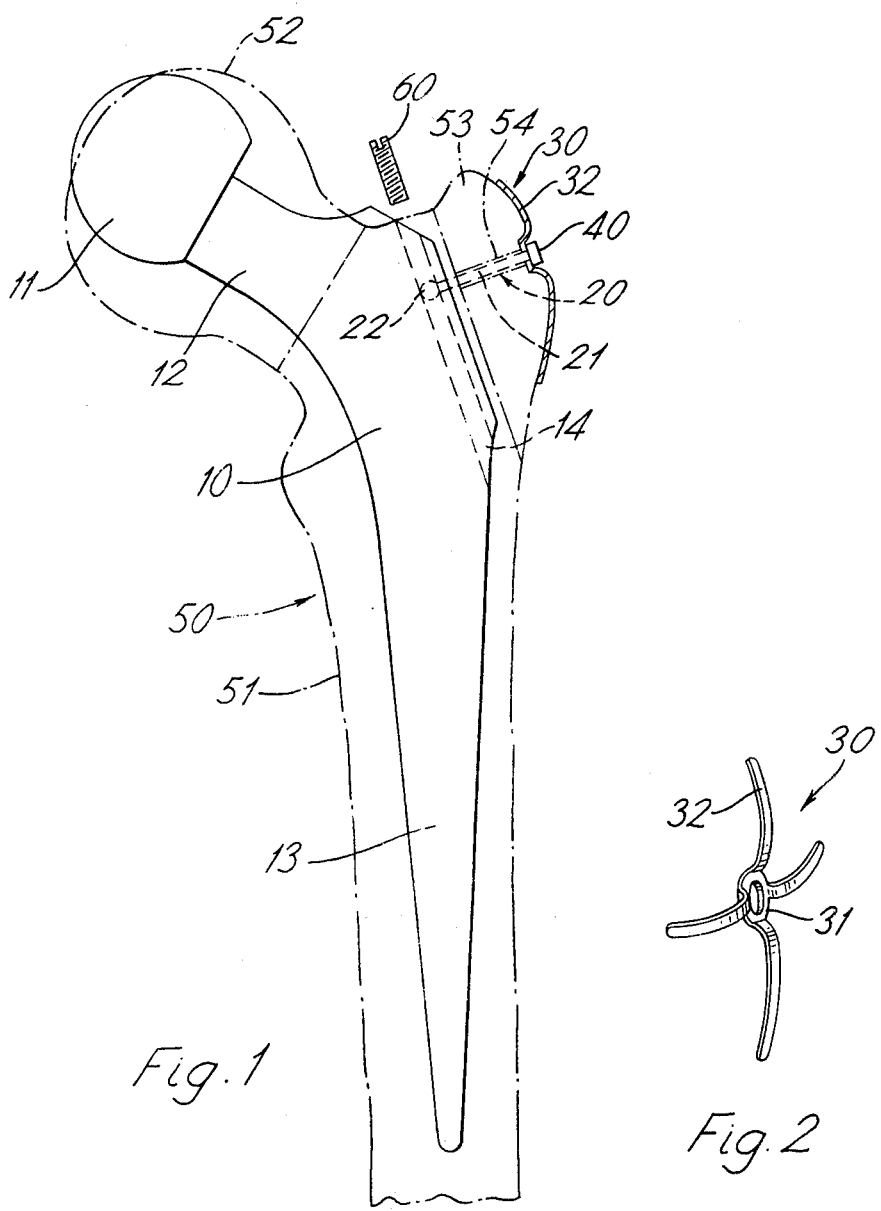

United States Patent [19]
Lee et al.

[11] 3,939,498
[45] Feb. 24, 1976

[54] ENDOPROSTHETIC FEMORAL HEAD

[75] Inventors: Alan John Clive Lee; Robin Sydney Mackwood Ling, both of Devon, England

[73] Assignee: National Research Development Corporation, London, England

[22] Filed: May 28, 1975

[21] Appl. No.: 581,475

[30] Foreign Application Priority Data
May 29, 1974   United Kingdom............... 23794/74

[52] U.S. Cl. ............................. 3/1.913; 128/92 CA
[51] Int. Cl.² ............................................ A61F 1/24
[58] Field of Search ........................... 3/1.9–1.913, 3/1; 128/92 CA, 92 C, 92 R, 92 BC

[56]   References Cited
UNITED STATES PATENTS

| 3,486,500 | 12/1969 | Ball et al. .......................... 128/92 R |
| 3,793,650 | 2/1974 | Ling et al. ............................. 3/1.91 |
| 3,859,669 | 1/1975 | Shersher .................................... 3/1 |
| 3,875,936 | 4/1975 | Volz ............................... 128/92 CA |

FOREIGN PATENTS OR APPLICATIONS

| 1,278,359 | 10/1961 | France .......................... 128/92 CA |
| 1,215,737 | 12/1970 | United Kingdom ........... 128/92 CA |

*Primary Examiner*—Ronald L. Frinks
*Attorney, Agent, or Firm*—Cushman, Darby & Cushman

[57]   ABSTRACT

An endoprosthetic femoral head device comprising a ball-shaped head connected, by way of a necked portion, to the wider end of a tapered intramedullary stem is modified to facilitate implantation involving detachment and re-attachment of the greater trochanter. The modification comprises the provision of a slot which extends longitudinally along the wider end of the stem, is open at one end, and has an interior width greater than that of its longitudinal mouth. A bolt-like member is adjustably located by its head in this slot with its shaft projecting from the device for passage through a bore formed in the detached trochanter. The trochanter is thus relocated and is secured by a fastener on the shaft free end. Preferably a spider-form washer with spring legs is located between the trochanter and fastener, and a screw-in plug is applied to the slot to positively locate the bolt head.

5 Claims, 2 Drawing Figures

U.S. Patent  Feb. 24, 1976  3,939,498

ENDOPROSTHETIC FEMORAL HEAD

This invention concerns endoprosthetic devices and more particularly such devices as used for replacing the femoral head in partial or total hip joint arthroplasty.

The usual form of endoprosthetic femoral head device comprises a ball-shaped head connected, by way of a necked portion, to the wider end of a tapered intramedullary stem which serves for securement of the device. One surgical procedure for use of such a device involves detachment and re-attachment of the greater trochanter, and this offers advantage in exposure of the site to receive the device and obviation of the need to detach muscular and ligamentous connections to the trochanter. However, the merits of this procedure are off-set by the fact that the necessary trochanteric re-attachment involves wired connections which many surgeons do not favour.

It has been proposed that this difficulty be reduced by the addition to the device of a bolt extending from the wider end of its stem whereby the trochanter can be bored, received over the bolt, and secured with a nut. However, in this modified device the bolt is fixed in a predetermined position relative to the stem with the result that a range of the modified devices, with differing bolt locations, must be made available to take account of the varying situations which can arise with different patients.

An object of the present invention is to reduce the difficulties of this situation by providing a further modified device which facilitates trochanter re-attachment. To this end the present invention provides an endoprosthetic femoral head device comprising the combination of a component including a ball-shaped head connected, by way of a necked portion, to the wider end of a tapered intramedullary stem, said wider end having a slot formed longitudinally therein, which slot is open at one end and has an interior width greater than that at its longitudinal mouth; an elongate member enlarged at one end for receipt in said slot at said open end thereof and captive movement therealong with the remainder of such member projecting transversely from said slot; and a fastener for connection around the other end of said member.

Use of the present device is generally similar to that of the above-mentioned modified device, but is advantageous in that the position of the elongate member is adjustable relative to the device stem and can suit different requirements.

Connection of the elongate member and fastener can be effected by screw connection in similar manner to the previously modified devices, or in other ways such as by crimping or cold welding. In either case, it may be desirable to inhibit translatory movement of the trochanter, and the elongate member therewith along the slot, under muscular action and this can be effected by the use of a bolt threadably received in the stem slot.

In order that the present invention may be more fully and clearly understood, the same will now be described by way of example with reference to the accompanying drawings, in which:

FIG. 1 schematically illustrates one form of device according to the invention, and FIG. 2 illustrates part of FIG. 1 in more detail.

The device illustrated in FIG. 1 comprises a main component 10 of integral metal construction having a ball-shaped head 11 connected through a necked portion 12, to the wider end of a tapered intramedullary stem 13. As is usual with such components, the longitudinal axis is curved or angled as it progresses through the neck portion into the stem. However, unlike the usual form of such components, the head is laterally off-set on the neck portion, and the neck portion joins the stem without the provision of a flange, this more particular form of the component being preferred for the reasons discussed in copending British Pat. application No. 44709/71.

For the purpose of the present invention, this component is formed with an open-end slot 14 extending longitudinally along the wider end region of the stem, the slot being located along the outermost face of this region relative to the associated angling or curvature thereof. This slot has an interior width greater than that of its longitudinal mouth, and has a circular or other bulbous cross-sectional shape which is longitudinally exposed by a relatively narrow entry.

The slot 14 is associated with an elongate member 20 constituted by a shaft 21 with an enlarged end portion 22, the latter portion being slidably receivable in the slot from either open end thereof while the shaft projects transversely from the slot.

The member 20 is associated, in turn, with a washer 30 and a fastener 40.

As shown separately in FIG. 2 the washer 30 preferably has an apertured central body portion 31 which is concavely dished towards its aperture, and a plurality of spring portions 32 extending radially from the central body portion to form an overall spider shape. As seen in FIG. 1, the spring portions are curved in the opposite sense to the central body portion dishing.

The fastener 40 can take different forms as indicated above and discussed hereinafter.

Use of the device is illustrated by FIG. 1 which schematically indicates in broken outline the femur at 50, with the femoral shaft, head and greater trochanter being respectively denoted at 51, 52 and 53. The intended use involves: exposure of the proximal femur, with the trochanter 53 being detached for this purpose; removal of the femoral head 52; application of the component 10 by securement of the stem 13 in the medullary canal of the shaft 51; the provision of a bore 54 in the trochanter; receipt of the enlarged portion 22 of the member 20 in the slot 14 with the associated shaft 21 projecting from the slot; re-location of the trochanter with the bore 54 receiving the shaft 21; application of the washer 30 over the free end of the shaft 21; and securement of the fastener to the shaft free end.

It is desirable that the trochanter be held under compression when re-located and this can be effected by use of the fastener 40 as a nut and the shaft as a co-operating bolt. As an alternative, the fastener can be adapted for crimped or cold-welded connection to the shaft. In either case a bolt 60 is preferably threadably received in the upper end of the slot to inhibit upward movement of the trochanter after re-attachment under the action of the associated muscular forces thereon.

The dishing of the washer central portion 31 serves to seat the fastener 40 therein and to seat the washer in the trochanter bore, while the washer spring portions 32 serve to distribute the compressive load over the trochanter, the latter portions being shaped to conform generally to the shape and dimensions of the trochanter and to afford resilience.

It remains to consider the materials to be employed in manufacture of devices according to the invention. The illustrated component 10 has been described as of integral metal construction, this being conventional for currently available femoral head devices. Also, it will be normally appropriate for reasons of mechanical strength for the member 20 to be of similar metal. In these circumstances it may be appropraite to employ a washer or slide cartridge of plastics material to separate the member head 22 from the wall of the slot 14, and thereby to obviate the possibility of corrosion between the metal parts which would otherwise be directly engaged, and also to afford low friction sliding capability as is currently preferred in endoprosthetic articulatory bone joint devices. Also, use of a plastics material may be appropriate for the bolt 60, when used, in order to avoid the possibility of crevice corrosion at the interface of this screw and the slot. A plastics material bolt 60 is also more readily cut to a desired length to locate the ball 22 without projection of the bolt from the slot 14. It may also be appropriate to employ plastics material between the fastener 40 and shaft 21.

We claim:

1. An endoprosthetic femoral head device comprising:

a component including a ball-shaped head connected, by way of a necked portion, to the wider end of a tapered intramedullary stem, said wider end having a slot formed longitudinally therein, which slot is open at one end and has an interior width greater than that at its longitudinal mouth;

an elongate member enlarged at one end, said one end being engaged in said slot at said open end thereof and captively movable therealong with the remainder of such member projecting transversely from said slot;

and a fastener connected around the other end of said member.

2. A device according to claim 1 wherein the longitudinal direction of said necked portion is angled relative to that of said stem at its narrower end, and said slot extends along said stem in the outside area thereof relative to the included angle between said necked portion and stem narrower end.

3. A device according to claim 2 further comprising a washer of overall spider form having an apertured central body portion located around said elongate member between said component and said fastener, and a plurality of spring portions extending generally radially from said body portion, said spring portions being similarly curved towards said component.

4. A device according to claim 3 wherein said body portion is dished towards its aperture and said component, and said spring portions are curved in the opposite sense to that of said dishing.

5. A device according to claim 2 wherein the end of said slot nearer to said ball-shaped head is open and screw-threaded, and further comprising a bolt threadably engageable with such threaded slot end.

* * * * *